United States Patent
Majlessi

(10) Patent No.: US 7,163,547 B2
(45) Date of Patent: Jan. 16, 2007

(54) HARVESTER

(76) Inventor: Heshmat Majlessi, 233 Purchase St., Rye, NY (US) 10580

( * ) Notice: Subject to any disclaimer, the term of this patent is extended or adjusted under 35 U.S.C. 154(b) by 489 days.

(21) Appl. No.: 10/359,607

(22) Filed: Apr. 23, 2003

(65) Prior Publication Data

US 2004/0215226 A1    Oct. 28, 2004

(51) Int. Cl.
*A61B 17/22*    (2006.01)
(52) U.S. Cl. ...................................... 606/159
(58) Field of Classification Search ............... 606/159, 606/151, 157, 158, 190, 210, 1
See application file for complete search history.

(56) References Cited

U.S. PATENT DOCUMENTS 5,133,360 A * 7/1992 Spears .................. 600/567
6,193,653 B1 * 2/2001 Evans et al. ................ 600/210
6,328,749 B1 * 12/2001 Kalmann et al. ............ 606/159

* cited by examiner

*Primary Examiner*—Kevin T. Truong
(74) *Attorney, Agent, or Firm*—Myron Greenspan; Lackenbach Siegel, LLP

(57) ABSTRACT

A device is disclosed to remove veins from the body. These can be unwanted varicose veins or healthy veins of the arms and legs used for bypasses or fistula formation. This device has a handle for the purpose of rotation and advancement of the instrument. This handle is attached to an elongated semi rigid shaft of various lengths. At the remote end of this shaft is the tip of the instrument comprised of a cylindrical shape device with an outward angle of various degrees. This tip is advanced with rotational move around the vein to separate the vein from surrounding tissue and also to cut the tributaries without damaging the wall of the vein. The shaft can be hollow to allow insertion of a long needle for the purpose of injection and local anesthesia.

22 Claims, 5 Drawing Sheets

HARVESTER

BACKGROUND OF THE INVENTION

1. Field of Invention

The invention generally relates to medical devices and more specifically to a device for removal of veins from body.

2. Description of the Prior Art

Patients undergoing cardiac or lower extremity bypass usually require saphenous vein harvesting. This is performed under anesthesia by making multiple incisions from the groin down to the lower part of the leg. Some physicians prefer a single long incision over the saphenous vein. However, complications from this approach are well documented in medical literature. Pain, swelling, infection under large skin flaps and more importantly, skin necrosis are just to name a few. Long hospital stay predisposes patients to pulmonary infections and thrombophlebitis. Many law suits arise from these complications. It is estimated that the complications add over 2 billion dollars to health care costs annually. A device which can accomplish the task of removing the desired veins without causing these complications will help patients.

In a typical case of stripping of unwanted varicose veins of legs, the saphenous vein is stripped by using External or internal stripper. Both procedures are usually performed at a hospital under anesthesia. Patients are left with multiple large unsightly incisions in their legs and also an undesirable and aesthetically repugnant cosmetic outcome. Pain and damage to the saphenous nerve are also a common occurrence.

Balloon dissecting instrument described in U.S. Pat. No. 5,944,734 are too complex, expensive and would require major anesthesia. In U.S. Pat. No. 5,893,858 a trocar system is disclosed to remove unwanted veins by simultaneously rotation and suction of these veins through multiple small incisions. In U.S. Pat. No. 5,843,104 an elongated tube is used using invagination technique. In U.S. Pat. No. 5,611,357 a technique is disclosed for removal of the veins using multiple incisions and sutures. U.S. Pat. No. 6,402,745 discloses an intravenous electrode for vein ablation. U.S. Pat. No. 5,792,168 describes a needle device to remove veins through multiple incisions.

SUMMARY OF THE INVENTION

This invention provides a surgical device that is adapted to remove healthy, as well as, unhealthy veins from the body.

The instrument presents a minimally invasive method to perform these tasks with virtually no disabilities.

The proposed instrument will be used for the same procedure of removing veins but under local anesthesia, in an office setting with patients resuming their work and activities immediately. Patients will not need any prescription pain medication because the groin incision is virtually pain free. This can reduce the cost of varicose veins surgery as well as bypass procedures.

It is a primary objective of this invention to harvest the long saphenous vein or other veins such as cephalic vein for the purpose of coronary or peripheral vascular bypass.

It is another object of the invention to remove the veins without damaging the veins themselves.

It is yet another object of this invention to create minimal pain, complication and disability following vein surgery.

This surgical apparatus comprises a handle, an elongate shaft and a tip. It also contains an elongate needle with a locking mechanism for the purpose of injection. The device can be manufactured from plastics, metals or both.

The handle of this surgical apparatus provides a firm grip for the purpose of rotation and advancement of the instrument. The shaft connects the handle to the tip of the instrument. This handle can be solid or hollow allowing passage of an elongate needle. The tip of the instrument is cone shaped and has an outward angle. This allows separation of the wall of the vein from the surrounding tissue without damaging the vein itself. The circular blade at the tip of the instrument can have a beveled angle of varying degrees to facilitate advancement of the instrument.

A side opening of the tip of the instrument allows percutaneous access for division of the vein.

Slits, grooves or generally V-shaped notches on the tip of the circular knife allow trapping of the venous tributaries and division far from the main venous structure. The V shaped openings act like a scissor facilitating divisions of the branches.

An elongate needle has a locking mechanism which allows it to be kept in a locked position, with the tip of the needle hidden within the instrument. The proximal end of this elongate needle can be unlocked and advanced through the handle of the instrument. This maneuver will advance the tip of the needle through the distal tip allowing injection of local anesthetic.

BRIEF DESCRIPTION OF THE DRAWINGS

The structure and operation of this device is best understood with the accompanying drawings and descriptions.

DESCRIPTION OF THE PREFERRED EMBODIMENTS

Figure 1:
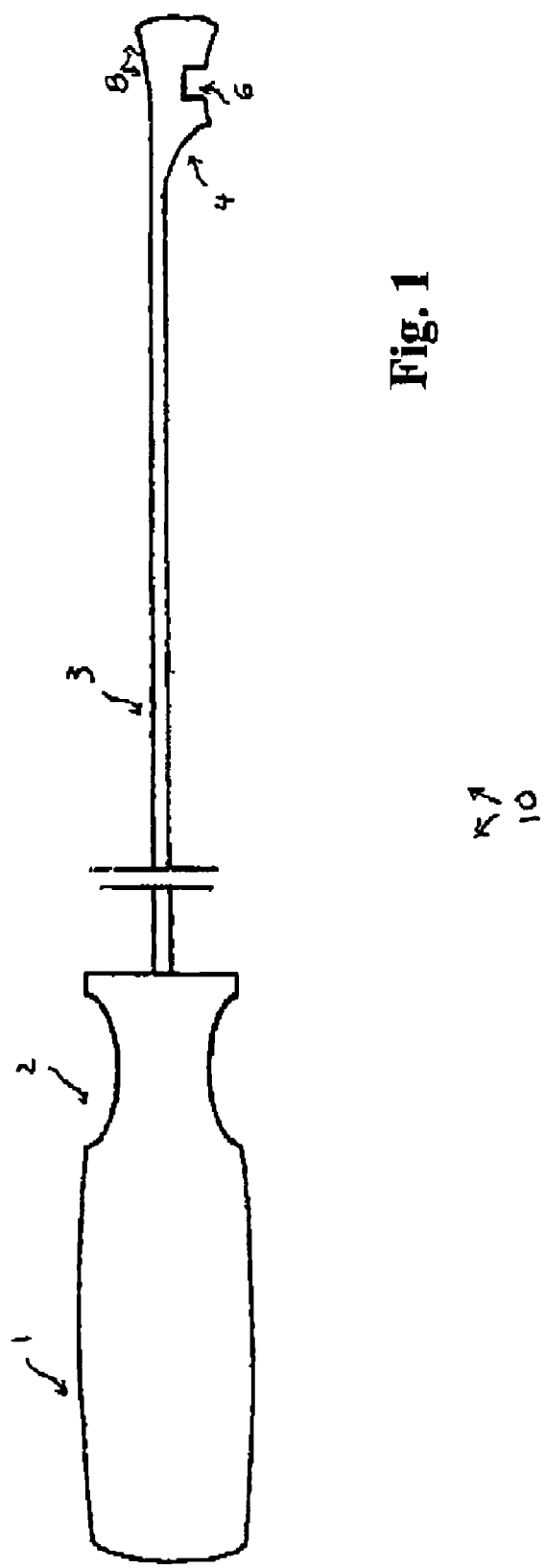
FIG. 1 is a schematic side elevational view of the surgical instrument in accordance with the invention.

This surgical device, a harvester, is generally designated by the reference number 10.

The device 10 includes a handle 1 to facilitate the holding of the instrument by the user and also to rotate and advance the device.

The handle is ergonomically designed, at 2, to facilitate firm gripping. Attached to this handle is an elongate shaft 3 of the instrument. The shaft is semi rigid shaft and can be solid and/or hollow to allow the insertion of a needle catheter or canula C through channel 20. The proximate end of the shaft 3 is attached to the handle 1 and the remote end is attached to a tip 5. The instrument 10 can be made of any suitable plastic such as PVC or metal such as stainless steel or a combination of the two which renders the instrument inexpensive and disposable.

Figure 2:
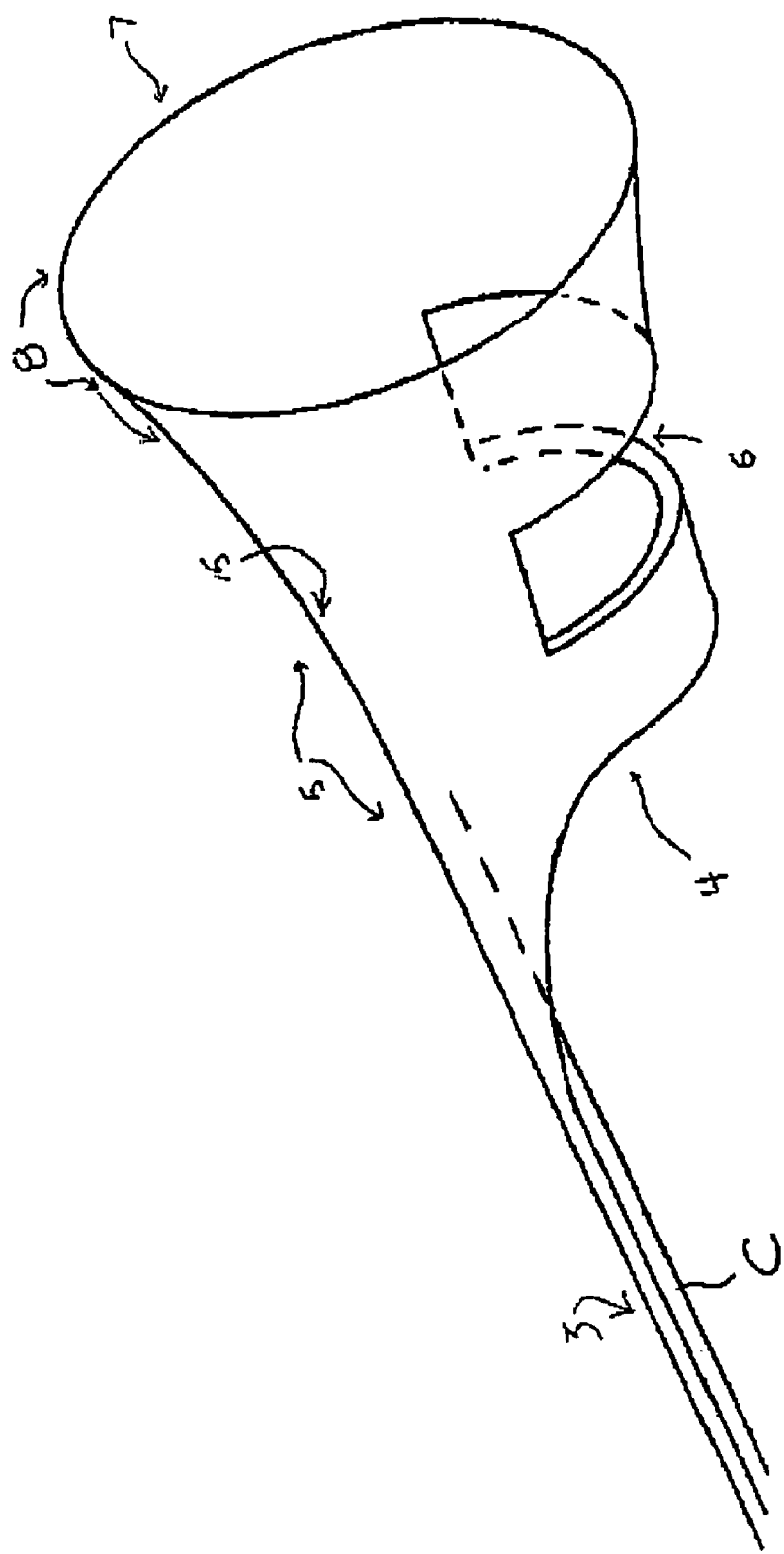
FIG. 2 is an enlarged perspective view of the tip of the instrument shown in FIG. 1 with the outward angle of the circular blade and the side opening.
Figure 3:
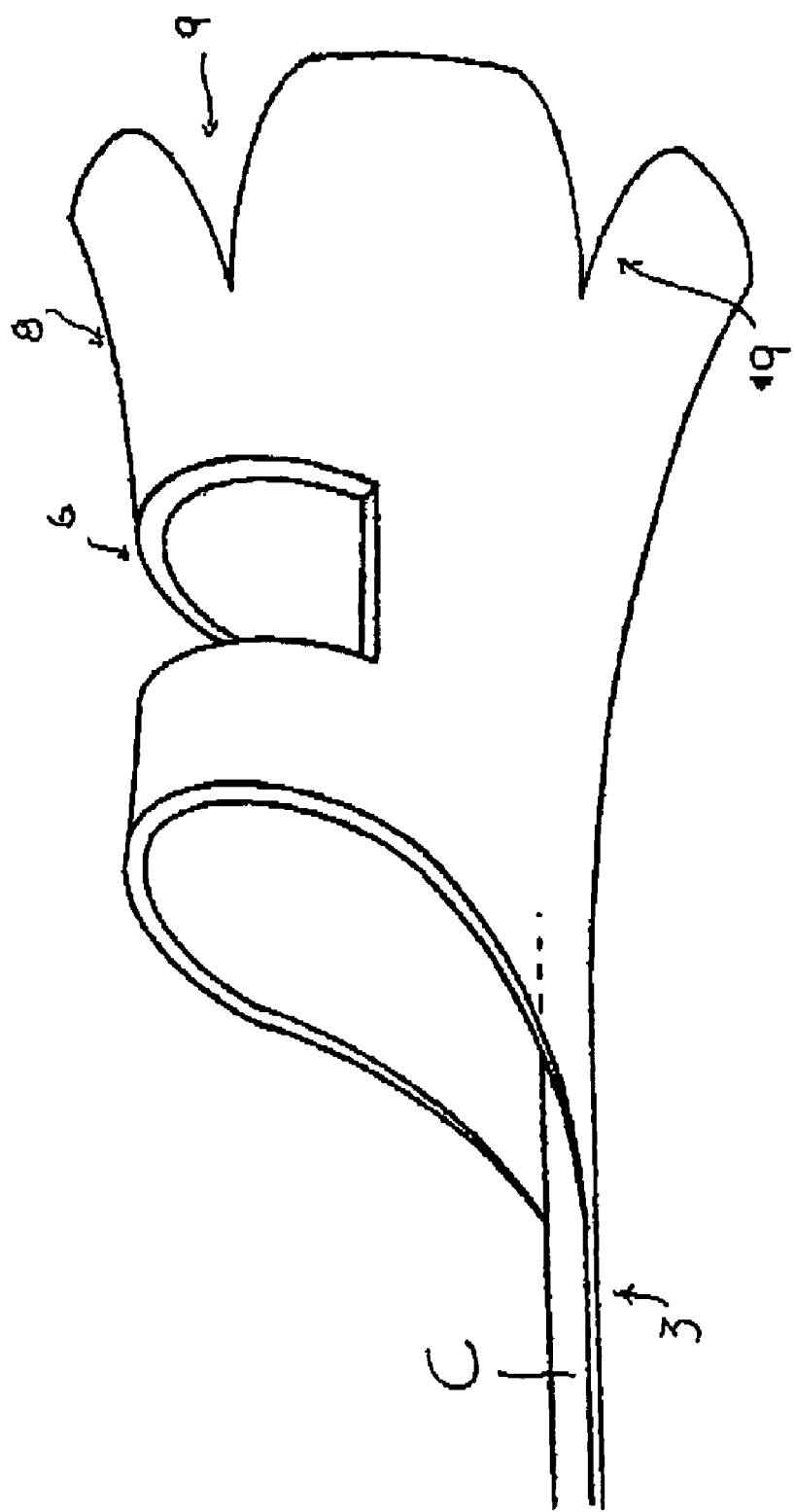
FIG. 3 is similar to FIG. 2 but shows the slots, grooves or notches on an alternate embodiment of the circular blade.

In FIG. 2 the tip 5 of the instrument is shown in a position relative to the shaft 3. Details of the tip are shown in FIG. 2 indicating an outward angle 8 of the tip approximately 20 to 30 degrees.

Cutting element 7 allows circular division of tissues and tributaries surrounding the vein without damaging the vein itself. The opening 6 on the side of the tip allows percutaneous division of the vein using a small caliber blade. The inner surface 15 of the tip opposite this opening 6 prevents damage to the tissue outside the instrument.

In an alternate embodiment the circular blade 7 can have several cutting slits, grooves or V-shaped notches 9 to allow trapping of the tributaries and division of these branches. These slits, grooves or V-shaped notches 9 are wide at the distal end and narrow in the direction of the proximal end. This progressive narrowing acts like a scissor to facilitate division of the branches.

Figure 4:
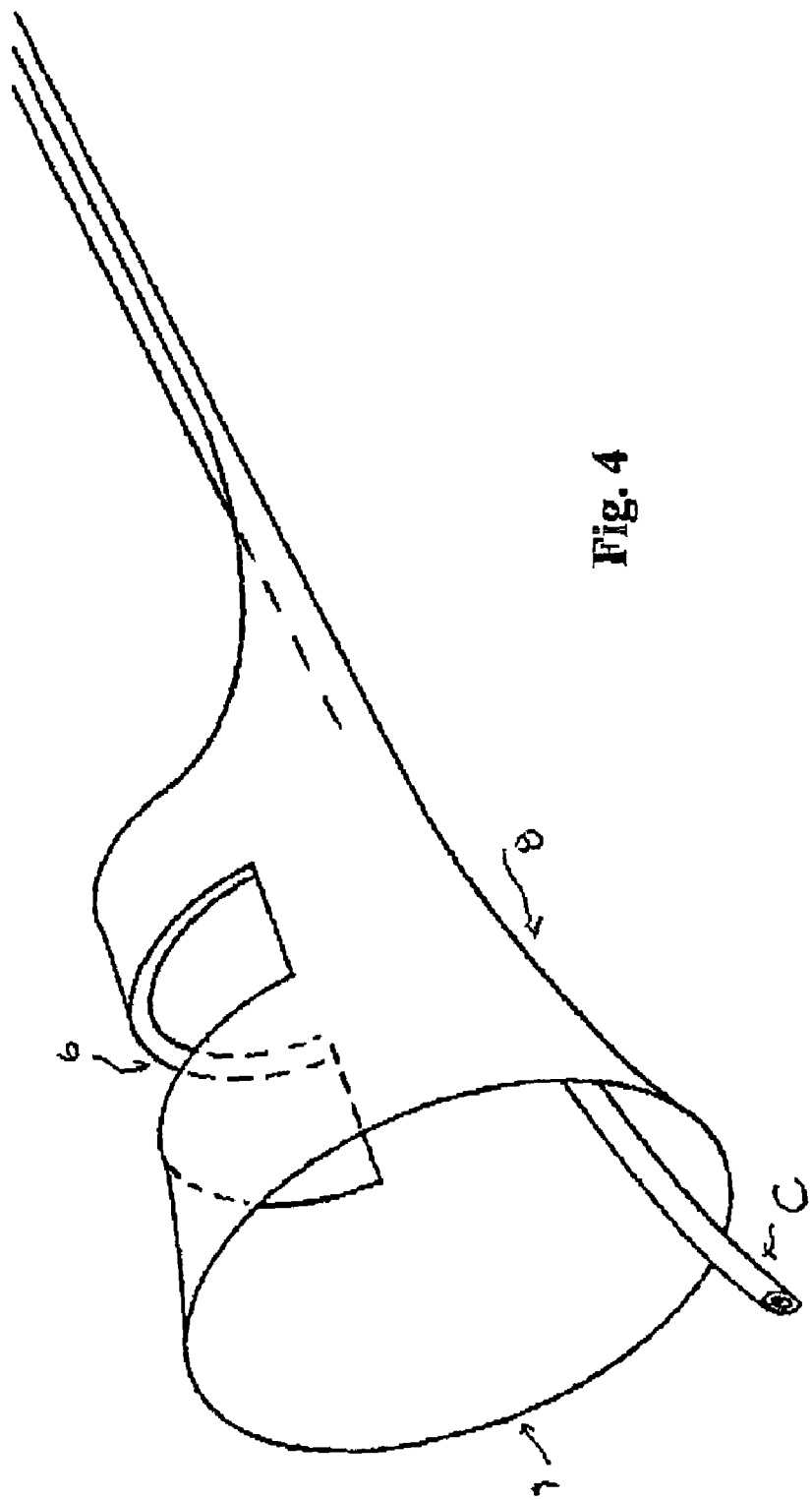
FIG. 4 is also similar to FIG. 2 but shows an the elongated needle within the tip of the instrument.
Figure 5:
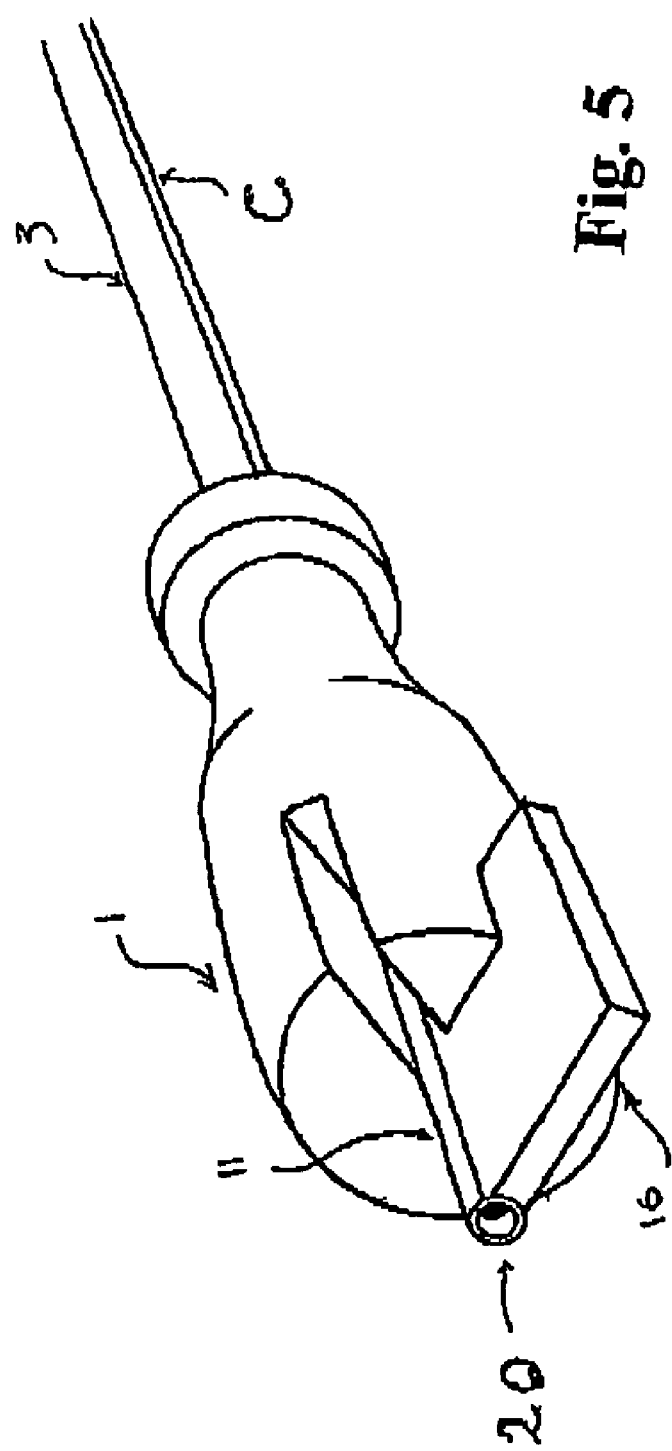
FIG. 5 is a schematic perspective view of a handle of the instrument, demonstrating the position of a shaft within the handle and also the proximal arm of the needle used to lock or unlock the elongate needle.

Referring to FIG. 4 the details are shown of the hollow needle C which has been advanced beyond the tip for the purpose of injection. There can be one or more needles for this purpose. This needle is normally in a locked position with the handle 16 of the needle located at the proximate surface of the instrument. Advancement of the needle C can be achieved by rotating and unlocking the handle or tab 16 and advancing the needle on the aide of the handle.

The operation of the surgical device will now be described. An incision is made in the groin of the patient over the saphenofemoral junction. This location is almost at the middle of the groin medial to the femoral pulse. The saphenous vein and the junction to the femoral vein are identified. All branches are divided and tied with the appropriate sutures. The saphenofemoral junction is divided and tied on the femoral side. The proximal end of the saphenous vein is grasped with an instrument and is passed through the opening at the tip of the instrument. Then the harvester is advanced by gentle pressure and rotation of the handle in order to separate the saphenous vein the surrounding tissue. All branches are divided spontaneously with the circular knife. Large branches are caught in the slits located at the distal end of the tip and severed. The outward angle of the tip and the blade prevents damage to the wall of the saphenous vein. The instrument is advanced as far as needed and the distal end of the vein severed using a percutaneous blade. This blade is inserted through the skin by palpation, dividing the vein through the side opening 6. It is generally advised not to go beyond the medial knee to avoid damaging the saphenous nerve. Hemostasis is achieved by gentle external pressure for a few minutes. All wounds are closed with appropriate fine subcuticular sutures.

The same steps can be applied for veins of the upper extremity such as cephalic vein. This procedure can be done under anesthesia, allowing immediate ambulation following surgery. Use of this instrument has several advantages over current techniques:

A) It allows immediate ambulation of the patient.
B) The patient will not require prescription pain medication.
C) It reduces hospital stays following bypass procedures and stripping.
D) it should virtually eliminate chances of skin necrosis, which is a common occurrence following present techniques.
E) it will reduce malpractice lawsuits resulting from above mentioned complications.
F) It will allow earlier discharge following cardiac bypass and peripheral arterial bypass procedure.
G) Lengthy surgical procedures will change into short outpatient/office procedures.

The invention claimed is:

1. A surgical device for removing veins from the body of a patient comprising a handle suitable for being gripped; an elongate shaft attached to said handle at a proximate end thereof and having a remote end; a cutting tip at said remote end, said cutting tip having a generally annular blade having a diameter greater than the diameter of a vein to be removed and defining an axis generally parallel to the length direction of said elongate shaft, said cutting tip having a cutting edge most remote from said handle generally facing a direction away from said handle for encircling and severing the vein to be removed from surrounding tissue by advancing the device with the vein received and passing through said annular blade, said cutting tip being in the form of an annular wall that tapers outwardly in a direction away from said handle.

2. A surgical device as defined in claim 1, wherein said handle has a diameter greater than the transverse dimensions of said shaft and is arranged generally in-line with the length direction of said shaft.

3. A surgical device as defined in claim 1, wherein said shaft is solid.

4. A surgical device as defined in claim 1, wherein said shaft is hollow.

5. A surgical device as defined in claim 4, further comprising a needle in the region of said cutting tip mounted for movement generally along the direction of said shaft between a first retracted position within said cutting tip and an extended position in which said needle extends beyond said cutting tip to inject or administer medicaments into tissue downstream of the cutting operations.

6. A surgical device as defined in claim 5, further comprising control means for selectively moving said needle between said retracted and extended positions.

7. A surgical device as defined in claim 6, wherein said control means comprises a gripping element in the region of said handle and an elongate control cable coupling said gripping element and said needle.

8. A surgical device as defined in claim 7, wherein said control cable extends through said hollow shaft.

9. A surgical device as defined in claim 7, further comprising locking means for locking said needle in one of said extended or retracted positions.

10. A surgical device as defined in claim 9, wherein said locking means comprises an elongate channel extending through said handle and generally coextensive with said hollow opening in said shaft, said control cable extending through said channel; and a locking member attached to said control cable and positionable between a first axial position more remote from said cutting tip and a second axial position more proximate to said cutting tip, whereby movement of said locking member to one of said axial positions locks said needle in one of said retracted and extended positions.

11. A surgical device as defined in claim 10, wherein said handle has a longitudinal slot and said locking member has a generally flat configuration receivable in said longitudinal slot, said locking member being movable downstream of said handle to said second axial position only when said locking member is aligned with said longitudinal slot.

12. A surgical device as defined in claim 1, wherein said cutting tip has a generally conical configuration.

13. A surgical device as defined in claim 12, wherein said conical configuration flares or diverges outwardly in the direction away from said handle.

14. A surgical device as defined in claim 13, wherein said outward diverging taper defines an angle within the range of 20–30 degrees with the length direction of said shaft.

15. A surgical device as defined in claim 1, wherein a slot is provided within said annular wall.

16. A surgical device as defined in claim 15, wherein said slot extends partially circumferentially about said annular wall.

17. A surgical device as defined in claim 1, wherein said cutting edge is circular.

18. A surgical device as defined in claim 1, wherein said cutting edge is smooth and continuous.

19. A surgical device as defined in claim 1, wherein said cutting edge is provided with a plurality of generally V-shaped notches for trapping and severing tributaries and divisions of branches associated with the vein being removed.

20. A surgical device as defined in claim 1, wherein said annular blade forms a generally circular cutting edge arranged in a plane generally normal to said elongate shaft.

21. A surgical device as defined in claim 1, wherein said cutting tip has maximum radial dimension at a point most remote from said handle.

22. A surgical device for removing veins from the body of a patient comprising a handle suitable for being gripped; an elongate shaft attached to said handle at a proximate end thereof and having a remote end; a cutting tip at said remote end, said cutting tip having a generally annular blade having a diameter greater than the diameter of a vein to be removed and defining an axis generally parallel to the length direction of said elongate shaft said cutting tip having a cutting edge most remote from said handle generally facing a direction away from said handle for severing the vein to be removed from surrounding tissue by advancing the device with the vein received and passing through said annular blade, said cutting tip being in the form of an annular wall that progressively tapers outwardly in a direction away from said handle.

* * * * *